(12) United States Patent
Equils et al.

(10) Patent No.: US 8,828,950 B2
(45) Date of Patent: Sep. 9, 2014

(54) CASPASE INHIBITORS IN THE TREATMENT OF INFECTION-ASSOCIATED PRETERM DELIVERY

(75) Inventors: Ozlem Equils, Sherman Oaks, CA (US); Calvin Hobel, Palos Verdes Estates, CA (US); Charles F. Simmons, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1274 days.

(21) Appl. No.: 12/598,259

(22) PCT Filed: May 1, 2008

(86) PCT No.: PCT/US2008/062253
§ 371 (c)(1),
(2), (4) Date: Jul. 28, 2010

(87) PCT Pub. No.: WO2008/137567
PCT Pub. Date: Nov. 13, 2008

(65) Prior Publication Data
US 2010/0292174 A1 Nov. 18, 2010

Related U.S. Application Data

(60) Provisional application No. 60/915,360, filed on May 1, 2007.

(51) Int. Cl.
*A61K 39/42* (2006.01)
*C12Q 1/37* (2006.01)

(52) U.S. Cl.
CPC ........ *C12Q 1/37* (2013.01); *G01N 2333/96466* (2013.01); *G01N 2500/00* (2013.01)
USPC ...................................................... 514/21.9

(58) Field of Classification Search
None
See application file for complete search history.

(56) References Cited

U.S. PATENT DOCUMENTS

| | | | |
|---|---|---|---|
| 5,545,616 A | 8/1996 | Woodruff | |
| 6,201,118 B1 | 3/2001 | Robidoux et al. | |
| 6,559,304 B1 | 5/2003 | Robidoux et al. | |
| 6,632,962 B2 | 10/2003 | Golec et al. | |
| 6,689,784 B2 | 2/2004 | Bebbington et al. | |
| 6,703,500 B2 | 3/2004 | Robidoux et al. | |
| 6,800,619 B2 | 10/2004 | Charrier et al. | |
| 7,053,057 B2 | 5/2006 | Golec et al. | |
| 7,074,782 B2 | 7/2006 | Bebbington et al. | |
| 7,232,661 B2 | 6/2007 | Yoon | |
| 7,790,463 B2 | 9/2010 | Mor et al. | |
| 2004/0014063 A1 | 1/2004 | Batteux et al. | |
| 2007/0161125 A1 | 7/2007 | Rosenfeld et al. | |
| 2009/0226397 A1 | 9/2009 | Carter | |
| 2010/0137263 A1 | 6/2010 | Smith | |

FOREIGN PATENT DOCUMENTS

WO 2008137567 A1 11/2008

OTHER PUBLICATIONS

Braun et al. "Neuroprotection by a caspase inhibitor in acute bacterial meningitis." Nature Medicine, vol. 5, No. 3, Mar. 1999, pp. 298-302.*
Equils et al. "Chlamydia Heat Shock Protein 60 Induces Trophoblast Apoptosis through TLR4." The Journal of Immunology, vol. 177, No. 4, pp. 1257-1263. 2006.*
Kirschbaum et al. "Antibiotics in the treatment of preterm labor." American Journal of Obstetrics and Gynecology, vol. 168, No. 4, pp. 1239-1246. Apr. 1993.*
Rodriguez et al. "Systemic Injection of a Tripeptide Inhibits the Intracellular Activation of CPP32-1 ike Proteases In Vivo and Fully Protects Mice against Fas-mediated Fulminant Liver Destruction and Death." J. Exp. Med. vol. 184, pp. 2067-2072. Nov. 1996.*
Li et al. "The 3C Protease Activity of Enterovirus 71 Induces Human Neural Cell Apoptosis." Virology, vol. 293, pp. 386-395. 2002.*
Brydon et al. "Influenza A virus-induced apoptosis in bronchiolar epithelial (NCI-H292) cells limits pro-inflammatory cytokine release." J. Gen. Virology, vol. 84 No. 9 2389-2400. Sep. 2003.*
Lin et al. "Caspase activation in equine influenza virus induced apoptotic cell death." Veterinary Microbiology, vol. 84, Issue 4, pp. 357-365. Feb. 2002.*
Takizawa et al. "Recruitment of apoptotic cysteine proteases (caspases) in influenza virus-induced cell death." Microbiol Immunol. vol. 43, No. 3. pp. 245-252. 1999. Abstract only.*
Equils et al. "Pretreatment with Pancaspase Inhibitor (Z-VAD-FMK) Delays but Does Not Prevent Intraperitoneal Heat-Killed Group B *Streptococcus*-Induced PretermDelivery in a PregnantMouseModel." Infectious Diseases in Obstetrics and Gynecology, vol. 2009, pp. 1-8. 2009.*
Sciortino et al.. "The Gamma-2-Herpesvirus Bovine Herpesvirus 4 Causes Apoptotic Infection in Permissive Cell Lines." Virology, vol. 277, pp. 27-39. 2000.*
Equils et al. "Chlamydia Heat Shock Protein 60 Induces Trophoblast Apoptosis through TLR4." The Journal of Immunology, vol. 177, No. 4, pp. 1257-1263. 2006—copy provided in OA mailed Oct. 19, 2012.*
Li et al. "The 3C Protease Activity of Enterovirus 71 Induces Human Neural Cell Apoptosis." Virology, vol. 293, pp. 386-395. 2002—copy provided in OA mailed Oct. 19, 2012.*
Brydon et al. "Influenza A virus-induced apoptosis in bronchiolar epithelial (NCI-H292) cells limits pro-inflammatory cytokine release." J. Gen. Virology, vol. 84 No. 9 2389-2400. Sep. 2003—copy provided in OA mailed Oct. 19, 2012.*

(Continued)

*Primary Examiner* — Christina Bradley
*Assistant Examiner* — Kristina M Hellman
(74) *Attorney, Agent, or Firm* — Linda B. Huber; Nixon Peabody LLP

(57) ABSTRACT

Apoptotic processes induced by infection of, or injury to, fetal and placental tissues have been implicated in preterm delivery. Thus, modulation of apoptotis constitutes a strategy for improving pregnancy outcome in women with intrauterine infections. Caspase inhibitors, including the pancaspase inhibitor Z-VAD-FMK, can be used to prevent apoptosis and, thus, prevent preterm delivery. Accordingly, compositions and methods comprising caspase inhibitors for prevention of preterm delivery are provided.

6 Claims, 7 Drawing Sheets

(56) References Cited

OTHER PUBLICATIONS

Lin et al. "Caspase activation in equine influenza virus induced apoptotic cell death." Veterinary Microbiology, vol. 84, Issue 4, pp. 357-365. Feb. 2002—copy provided in OA mailed Oct. 19, 2012.*

Takizawa et al. "Recruitment of apoptotic cysteine proteases (caspases) in influenza virus-induced cell death." Microbiol Immunol. vol. 43, No. 3. pp. 245-252. 1999. Abstract only—copy provided in OA mialed Oct. 19, 2012.*

Bussen et al., Thyroid autoantibodies in euthyroid non-pregnant women with recurrent spontaneous abortions, Human Reproduction, Nov. 1995, vol. 10, No. 11, pp. 2938-2940.

Curry et al., First-trimester maternal plasma cytokine levels, pre-pregnancy body mass index, and spontaneous preterm delivery, Acta Obstet et Gynecol Scand. ePub Jan. 2009, vol. 88, No. 3, pp. 332-342.

Kalinka et al., Interleukin-1B and interleukin-1 receptor antagonist genes polimorphisms and the risk of spontaneous preterm delivery in the population of Polish women, Arch Perinatal Med, 2008, vol. 14, No. 4, pp. 33-36.

Romero et al., The natural interleukin-1 receptor antagonist prevents interleukin-1-induced preterm delivery in mice, Am J Obstet Gynecol., Oct. 1992, vol. 167, No. 4, Pt. 1, pp. 1041-1045; Abstract.

Skogstrand et al., Simultaneous measurement of 25 inflammatory markers and neurotrophins in neonatal dried blood spots by immunoassay with xMAP technology, Clinical chemistry, Oct. 2005, vol. 51, No. 10, pp. 1854-1866.

International Search Report and Written Opinion for International Application No. PCT/US10/59248 dated Apr. 12, 2011.

PCT/US2008/062253 Written Opinion dated Aug. 4, 2008.

PCT/US2008/062253 International Preliminary Report on Patentability Nov. 3, 2009.

Da Fonseca et al. Prophylactic administration of progesterone by vaginal suppository to reduce the incidence of spontaneous preterm birth in women at increased risk: a randomized placebo-controlled double-blind study. Am J. Obstet Gynecol. (2003). 188(2): 419-424. Absract.

Fortunato et al. Distinct molecular events suggest different pathways for preterm labor and premature rupture of membranes. Am J. Obstet Gynecol. (2001). 184(7):1399-405. Abstract.

Kumagai et al. Apoptosis in the normal human amnion at term, independent of Bcl-2 regulation and onset of labour. Mol Hum Reprod. (2001). 7(7):681-689.

Okun et al. Antibiotics for bacterial vaginosis or *Trichomonas vaginalis* in pregnancy: a systematic review. Obstet Gynecol. (2005). 105(4): 857-68. Abstract.

* cited by examiner (A) Negative Control (B) Positive Control (C) Media (D) HK-GBS (A) Negative Control (B) Positive Control (C) Media (D) HK-GBS

Figure 4

| Caspase 3 (32 kDA) → | | | — |
|---|---|---|---|
| GAPDH (38 kDA) → | — | — | — |
| | PBS | 5hr | 14hr |

(A) PBS (B) HK-GS (5 hr)

(C) HK-GS (14 hrs)

CASPASE INHIBITORS IN THE TREATMENT OF INFECTION-ASSOCIATED PRETERM DELIVERY

This application is the National Phase of International Application PCT/US08/62253, filed May 1, 2008, which designated the U.S. and that International Application was published under PCT Article 21(2) in English. This application also includes a claim of priority under 35 U.S.C. §119(e) to U.S. provisional patent application No. 60/915,360, filed May 1, 2007.

GOVERNMENT RIGHTS

The invention described herein arose in the course of or under NIH Grant No. M01-RR00425. The U.S. Government may thus have certain rights in this invention.

FIELD OF THE INVENTION

The invention relates to compositions and methods for the prevention of infection-associated preterm delivery in mammals. Specifically, caspase inhibitors are used to prevent apoptosis in placental and fetal membrane tissues.

BACKGROUND OF THE INVENTION

Preterm birth is the most common cause of death in newborn babies worldwide (Moss et al., 2002). In the US preterm delivery is one of the most significant complications of pregnancy. Approximately 34% of infant mortality is due to preterm delivery in the US (Callaghan et al., 2006). It has a high prevalence rate (11%), and about 40% (>$4 billion) of all infant health care expenditures in the US are related to prematurity.

Infection is the most common cause of preterm delivery and stillbirth globally. In the US infection plays a role in ~50% of total and 80% of early preterm deliveries (<32 weeks of gestation) (Lamont, 2003; Goldenberg et al., 2000). However, despite being one of the most important maternal-fetal problems, there are no effective prevention strategies or treatments for infection-induced preterm delivery, and there is no thorough understanding of the molecular mechanisms involved.

The traditional conception of preterm delivery has been that of an ordinary pregnancy progressing to term before the fetus is ready for delivery. In recent years this conception has come into question, and physicians are beginning to think of preterm delivery as a disease state caused by pathologies in the fetal/placental unit. It has thus been suggested that preterm delivery be considered a syndrome caused by multiple etiologies but ending in a common pathway (Bernstein, 2000). The present invention relates to one end pathway, namely apoptotic processes (programmed cell death) induced by infection or other injury to fetal/placental tissues.

Up to 80 percent of early preteen births (<32 weeks) are associated with intrauterine infection. Despite the link between intrauterine infection and preterm delivery, antibiotic treatment of women with intrauterine infection is not uniformly protective. In fact, some clinical trials of antibiotic treatment of intrauterine infections have been associated with worse outcomes. These seemingly inconsistent results are likely due to the fact that the apoptotic processes triggered by the infection, rather than the infection itself, are responsible for the increased risk of preterm delivery.

It has been shown that microbial antigen treatment of primary human placenta cells (trophoblasts) and trophoblast cell lines leads to increased rates of apoptosis in these cells. Specifically, the inventors have recently shown that microbial antigens activate apoptotic machinery in the human placental cells (Equils et al., 2006) Moreover, mouse models of intrauterine infection and sepsis suggest that there is increased apoptosis in the placentas and membranes of the animals exposed to microbial antigens. This link between apoptosis, intrauterine infection and preterm delivery, in conjunction the failure of antibiotics to prevent preterm delivery, suggest that increased apoptosis is a factor in preterm delivery. Accordingly, there is a need for treatments that modulate the apoptotic pathway induced by intrauterine infection or other injury, rather than solely treating the infection itself.

SUMMARY OF THE INVENTION

The present inventive technology addresses the shortcomings of preventative preterm delivery treatments currently known in the art by providing means to mediate apoptotic pathways in placental and fetal membrane tissues. The inventive technology is based on the use of caspase inhibitors to stop apoptosis in placental and fetal membrane tissue. Accordingly, compositions and methods comprising caspase inhibitors to prevent apoptosis in placental and fetal membrane tissues and thereby preventing preterm delivery are provided.

BRIEF DESCRIPTION OF THE FIGURES

FIG. 4 shows that Intrauterine HK-GBS injection induces caspase 3 protein expression in the placenta as determined by Western blotting in a time-dependent fashion. Pregnant mice were euthanized 5 or 14 hours after HK-GBS exposure. Caspase 3 activation was assessed by performing western blot analyses for activated cleaved caspase 3. GAPDH expression served as the loading control. Representative data from three separate experiments are shown.

DETAILED DESCRIPTION OF THE INVENTION

Figure 1:
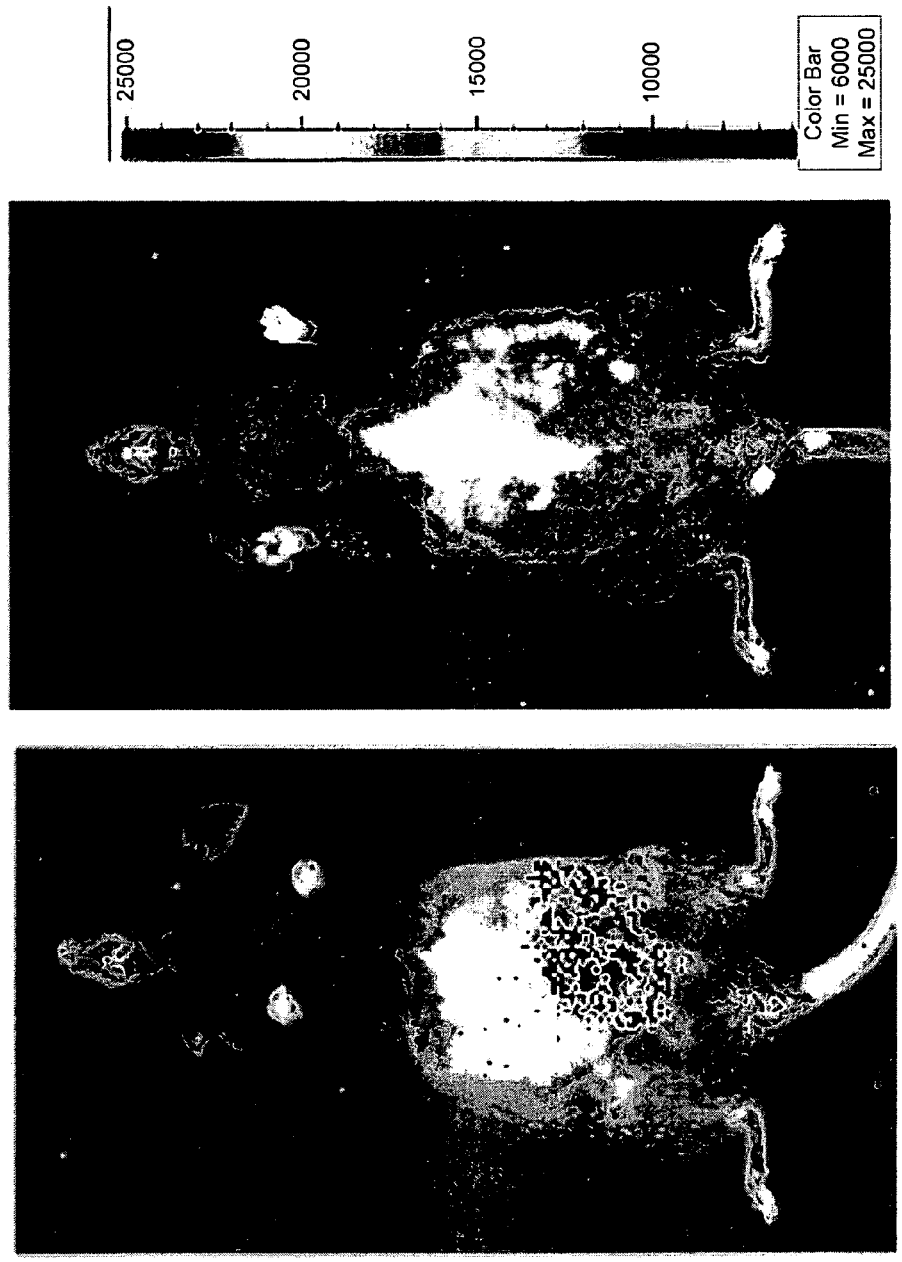
FIG. 1 shows images of control and treatment pregnant mice that are positive transgenics for a Cox2/luciferase construct. Both mice were injected with lipopolysaccharide, and the LPS injection resulted in abortion in the control mouse. However, the treatment mouse was given a pancaspase inhibitor prior to LPS injections and this resulted in maintenance of pregnancy.

All references cited herein are incorporated by reference in their entirety as though fully set forth.

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Therapeutically effective amount" as used herein refers to that amount which is capable of achieving beneficial results in a mammal susceptible to preterm delivery because of intrauterine infection. A therapeutically effective amount can be determined on an individual basis and will be based, at least in part, on consideration of the time of administration relative to the progression of the disease in addition to the characteristics of the therapeutic compound (including activity, pharmacokinetics, pharmacodynamics, and bioavailability), the physiological condition of the subject (including age, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

"Treatment" and "treating," as used herein refer to both therapeutic treatment and prophylactic or preventative measures, wherein the object is to prevent, slow down and/or lessen the disease state even if the treatment is ultimately unsuccessful.

In various embodiments, the present invention provides pharmaceutical compositions including at least a caspase inhibitor along with a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits. In addition, in various embodiments, the pharmaceutical compositions according to the invention may be formulated for delivery via any route of administration. "Route of administration" may refer to any administration pathway known in the art, including but not limited to aerosol, nasal, oral, transmucosal, transdermal, subcutaneous, or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

The inventors have found that treatment with pancaspase inhibitors, such as Z-VAD FMK (carbobenzoxy-valyl-alanyl-aspartyl-[O-methyl]-fluoromethylketone), reduces fetal mortality in pregnant mice receiving intraperitoneal injections of bacterial endotoxin (Lipopolysaccharide). Accordingly, caspase inhibitors (specific caspase inhibitors or pancaspase inhibitors) have a place in the treatment of pregnant women with intrauterine infection and prevention of preterm delivery. As one of skill in the art will recognize, a range of pancaspase inhibitors may be used in connection with alternate embodiments of the invention.

We have demonstrated in vivo through the use of a Xenogen CCD camera that intraperitoneal endotoxin (lipopolysaccharide) injection leads to pup mortality in the 14 day pregnant mouse, and that intraperitoneal treatment of these animals with a pancaspase inhibitor (Z-VAD-FMK) prior to LPS injection prevents pup mortality despite continued inflammation as assessed by Cox2 promoter activation (FIG. 1), wherein the continued inflammation is used as an indicator of persistent infection. Therefore, the use of caspase inhibitors confers a protective effect not seen by merely controlling infection through the use of antibiotics. As one of skill in the art will realize that the murine model can provide a guide to expected outcomes in human pregnancy, it is believed that caspase inhibitor treatment will be effective in the treatment of pregnant women with intrauterine infection so as to prevent preterm delivery and improve pregnancy outcome. This is a novel mammalian model for the improvement of pregnancy outcome.

Our experimental test method is based on the use of a mouse model in which inflammation (as assessed by Cox2 promoter activation) is detected optically by using a transgenic animal in which activation of the promoter results in synthesis of luciferase. When luciferin is subsequently injected, the presence of luciferase is detected by a sensitive camera as the production of light. The detected inflammation is indicative of the infection caused by the LPS injection.

In FIG. 1, pregnant mice are imaged. The mice were first mated with Cox2/luciferase males so that the pups would be positive for the Cox2/luciferase construct. The mice were treated with LPS which is normally produced by bacteria and results in inflammation. We injected pregnant mice with 0.1 microgram/ml LPS intraperitoneally (ip) for the control mice 0-24 hours (using a 2, 4, 6, 12 hour time course) prior to the imaging. The resulting inflammation causes the upregulation of Cox2 promoter in the pups resulting in the synthesis of luciferase. Prior to imaging the mice were injected with luciferin and the combination of luciferin and luciferase resulted in bioluminescence which was detected by the imaging system. The treatment mice were given 0.25 mg ip of the pancaspase inhibitor 5-30 minutes prior to each LPS injection.

In the case of the control mouse (right-hand side of FIG. 1) inflammation results in the abortion of the pups (no bioluminescence detected). However, when the mice are also treated with the pancaspase inhibitor (Z-VAD-FMK), the pups do not abort and can be detected as a bioluminescence signal which here has been superimposed over the black and white image (left-hand side of FIG. 1). The presence of the signal indicates that while the caspase inhibitor does not prevent inflammation, it does prevent abortion of the pups. Thus, in the case of inflammation resulting from infection (as is common in cases of preterm delivery in humans) effective treatment includes antibiotic to reduce or eliminate the infection and caspase inhibitor to prevent preterm delivery.

Group B *streptococcus* is one of the most common causes of neonatal infection and is associated with preterm delivery. Day 14.5 pregnant mice are used in a model of bacterially induced preterm delivery and it is shown that both intrauterine and intraperitoneal treatment with heat killed Group B *streptococcus* (HK-GBS) induces preterm delivery. We injected HK-GBS into the pregnant uterus and observed an increase in caspase 3 and m-calpain expression (a key intermediary in the caspase-independent apoptotic pathway) in the placenta. Apoptosis was confirmed by TUNEL assay and caspase 3 activation in the membranes and the placenta. Intraperitoneal (i.p.) treatment with Z-VAD-FMK, a global inhibitor of caspases, delayed i.p. HK-GBS-induced preterm delivery. One of skill in the art will realize that this model will be applicable to other bacterial infections shown to induce apoptosis in the placenta, for example infection by *Chlamydia trachomatis, E. coli* or mycoplasma.

One of skill in the art will also realize that many pancaspase inhibitors are known and that other known pancaspase inhibitors could be employed in the disclosed model. By way of example and not by way of limitation, the pancaspse inhibitors IDN-1965, zAsp-CH$_2$-DCB, PF-03491390, IDN-6556, and Q-VD-OPH and their pharmaceutical equivalents may be employed in the present model.

Materials and Reagents

Group B β-hemolytic *streptococcus* bacteria were grown to log phase at 37° C. in Trypticase Soy Broth (Becton Dickinson), concentrated by centrifugation, resuspended in phosphate buffered saline (PBS), quantified by plating serial dilutions and then heat-inactivated by boiling for 5 minutes. Bacterial killing was verified by lack of growth overnight in broth and solid media. Heat killed (HK)-GBS stock was aliquoted and frozen at −80° C. Before each experiment, a fresh vial of frozen heat killed bacteria was thawed, vortexed, diluted as necessary and used in the experiments. Z-VAD-FMK (BD Pharmingen catalog #550377) was dissolved in DMSO, aliquoted and stored at −80° C. and then diluted as needed in PBS for experiments.

Model of Infection-Induced Preterm Delivery in Mice

Timed-pregnant C57BL/6J mice (Jackson Laboratories, Bar Harbor, Me.) on day 14.5 of pregnancy were anesthetized with 0.015 ml/g body weight of 2.5% tribromoethyl alcohol and 2.5% tert-amyl alcohol in PBS. A 1.5 cm midline incision was made in the lower abdomen. The right uterine horn was identified and injected in its mid-section with either PBS or GBS ($10^9$ organisms) in a 100 µl volume delivered extraovularly between fetal sacs. The incision was closed with interrupted sutures of coated 4-0 polyglactin 910 sutures (Vicryl, Ethicon) at the peritoneum and wound clips at the skin. Surgical procedures lasted approximately 10 minutes. Animals were either observed through delivery or euthanized 5 or 14 hours after HK-GBS injection for tissue collection (placentas and membranes). These tissues were fixed in 10% neutral buffered formalin and embedded in paraffin for sectioning.

To assess whether caspase inhibition prevented HK-GBS-induced preterm delivery, unanesthetized day 14.5 pregnant CD1 mice (Harlan Laboratories, Madison, Wis.), which breed more effectively than inbred C57BL/6J mice, were pre-treated intraperitoneally with PBS, DMSO or the pancaspase inhibitor Z-VAD-FMK (10 mg/kg) 30 minutes prior to intraperitoneal injection with either $10^9$ HK-GBS bacteria or medium. There were no differences in delivery outcomes following intraperitoneal injection with GBS whether or not animals were pretreated with either PBS or DMSO (diluents for the caspase inhibitor). Therefore these separate control pre-treatments are combined for the analyses.

Post-operatively, mice were observed for premature delivery (defined as the finding of at least one pup in the cage or the lower vagina within 48 hours of microbial injection.

TUNEL Staining

Apoptosis was assessed by the in situ terminal deoxynucleotidyl transferase (TdT)-mediated dUTP nick end-labeling (TUNEL) technique with the TACS 2TdT Blue Label kit (Trevigen, Gaithersburg, Md., USA) according to the protocol supplied by the manufacturer. Positive control sections were pretreated with TACS-Nuclease to induce DNA fragmentation before the TUNEL reaction. Negative controls were processed in the absence of the TdT enzyme and showed no staining. Mouse ovaries were used as positive control tissues.

Immunohistochemistry

To assess caspase-3 and m-calpain expression, tissue sections were deparaffinized in xylene, rehydrated in ethanol solutions and rinsed in PBS. To facilitate antigen retrieval, sections were treated with Antigen Unmasking Solution (Vector Laboratories, Burlingame, Calif., USA) and heated in a pressure cooker for 10 min. Endogenous peroxidases were quenched in a 3% $H_2O_2$/methanol solution. After 40 minutes of blocking with a 1:20 solution of normal goat serum to PBS/Tween 20, sections were incubated overnight at room temperature in a 1:350 dilution of an antibody to either activated caspase-3 (R&D Systems, Minneapolis, Minn., USA) or m-calpain (GeneTex, Inc, San Antonio, Tex.). The sections were then rinsed in PBS and incubated for 45 minutes at room temperature with a biotinylated goat anti-rabbit immunoglobulin G secondary antibody (1:200; Vector Laboratories). Immediately after incubation with the secondary antibody, sections were incubated for 30 min at room temperature with avidin-biotin-peroxidase solution (Vectastain elite ABC kit; Vector Laboratories). The antigen was visualized with the NovaRed Substrate kit (Vector Laboratories) and counterstained with hematoxylin. Negative control sections were processed in the absence of the active caspase-3 primary antibody). Mouse ovarian sections containing atretic follicles were used as positive control tissues.

Western Blotting

Frozen mouse placentas were homogenized on ice in Ripa buffer (Sigma) supplemented with protease inhibitor cocktail. Tissue homogenates were centrifuged at 13,000 rpm for 20 minutes at 4° C. and the supernatants were collected. The protein concentration was determined using the Bio-Rad Bradford protein assay. Samples were diluted in sample buffer (10% glycerol, 0.0625M Tris-HCl, 5% β-mercaptoethanol, 2% sodium dodecyl sulfate, 0.05% bromophenol blue) and boiled for 10 minutes. Proteins (40-150 ug) were separated by electrophoresis through a 10% Tris-HCl polyacrylamide gel (BioRad, Hercules, Calif.) and then transferred to a polyvinyl difluoride membrane (Invitrogen, Carlsbad, Calif.). Membranes were blocked at room temperature for 1 hour in PBS containing 0.05% Tween 20 (PBST) and 5% nonfat milk/Tween 20 and then incubated overnight at 4° C. with a primary antibody [anti-M-Calpain, 1:1000 dilution (GeneTex, SanAntonio, Tex.), anti-Caspase-3, 1:200 dilution (Chemicon, Temecula, Calif.), or anti-GAPDH, 1:200 dilution (Santa Cruz Biotechnology, Santa Cruz, Calif.)]. The following morning, the membranes were washed 3 times in PBST and then incubated for 1 hour at room temperature with a horseradish peroxidase-conjugated anti-rabbit secondary antibody, 10 ug/ml (Pierce, Rockford, Ill.). After 3 more washes in PBST, the protein bands were visualized by chemiluminesence using the Super Signal West Dura substrate kit (Pierce) and exposed to BioMax film (Kodak, Rochester, N.Y.).

Analyses

Chi-square analysis was done to assess the effect of Z-VAD-FMK pretreatment on HK-GBS-induced preterm delivery.

Intraperitoneal inoculation with heat killed GBS ($10^9$) in day 14.5 pregnant mice induced preterm delivery (Table 1). No mother died during the course of the experiment. Similar results were obtained in animals exposed to intrauterine HK-GBS. These data confirm that HK-GBS exposure leads to preterm delivery in the mouse pregnancy model.

TABLE 1

Intraperitoneal HK-GBS injection leads to preterm delivery, and pre-treatment with Z-VAD-FMK delays preterm delivery in mice.

|  | Preterm Delivery (<24 hours) | Delivery <18 hr (%) | Delivery 18-24 hrs (%) |
| --- | --- | --- | --- |
| GBS (n = 14) | 12 (86%) | 12 (86%) | 0 |
| Z-VAD + GBS (n = 6) | 3 (50%) | 1 (17%) | 2 (33%) |
| p value | 0.13 | 0.0072 | 0.079 |

HK-GBS Injection Leads to Apoptosis in the Placenta and Membranes

Figure 2:
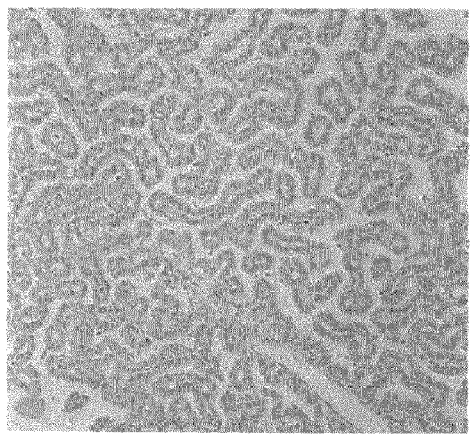
FIG. 2 shows that Intrauterine HK-GBS injection leads to TUNEL positive apoptosis in the membranes. 14.5 week timed pregnant mice were injected either with HK-GBS or PBS and euthanized at 5 or 14 hours to isolate the placenta and membranes. The section shown was obtained after 14 hours of stimulation. TUNEL positive apoptotic cells are stained black-brown. The slides were treated with PBS for the negative control (A); endonuclease for the positive control (B); and media (C) for baseline apoptosis levels.
Figure 2:
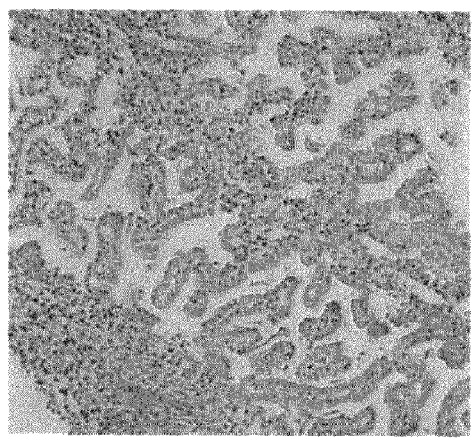
Figure 2:
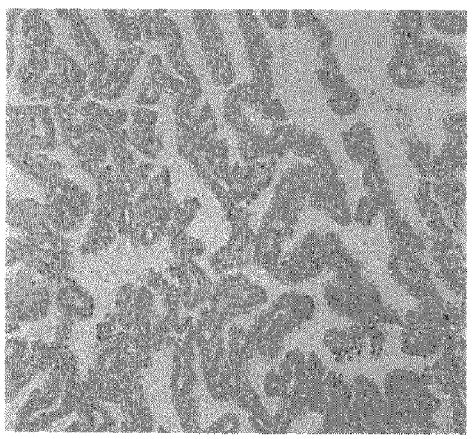
Figure 2:
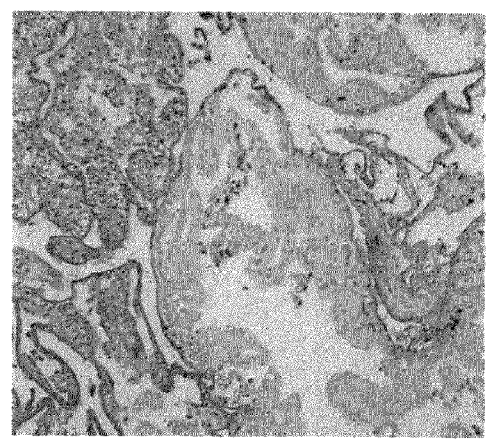

We used the TUNEL assay to assess the effect of HK-GBS exposure on placental and membrane apoptosis in day-14.5 pregnant mice euthanized at 5 (n=4) or 14 hours (n=6) after intrauterine injection with HK-GBS. There was TUNEL positive apoptosis in the membranes (FIG. 1) and in the placenta (FIG. 2).

Figure 3:
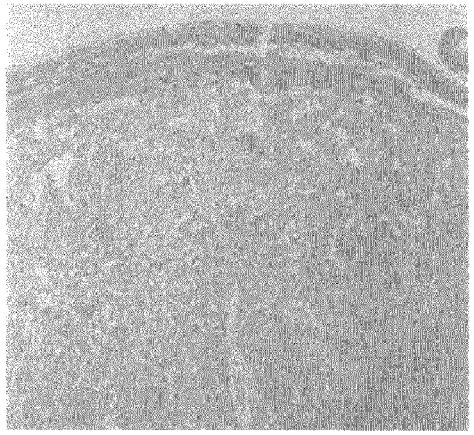
FIG. 3 shows that Intrauterine HK-GBS injection leads to TUNEL-positive apoptosis in the placenta. In the mouse placenta, there were no TUNEL positive cells at 5 hours. HK-GBS exposure led to an increase in TUNEL positive cells at 14 hours (D). The slides were treated with PBS for the negative control (A) and endonuclease for the positive control (B); and media for baseline apoptosis levels (C).
Figure 3:
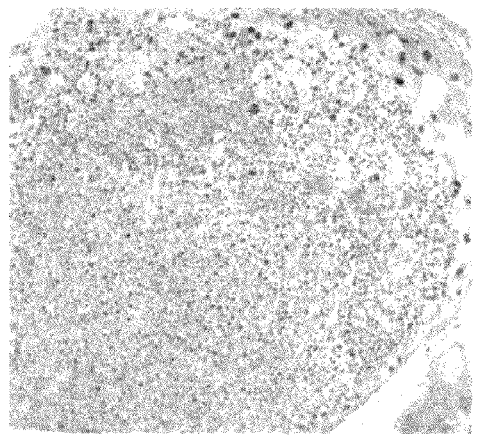
Figure 3:
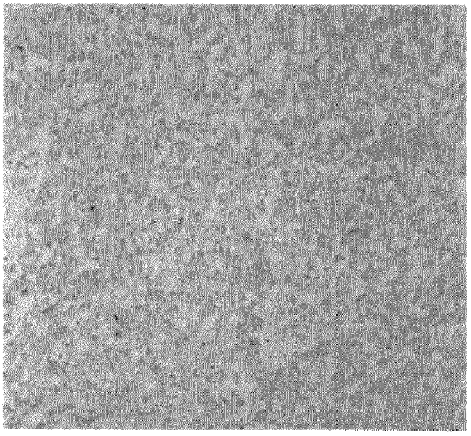
Figure 3:
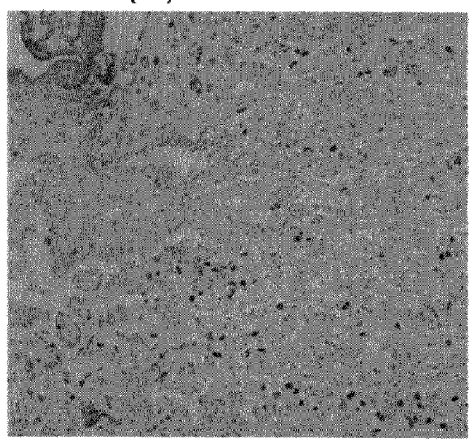
Figure 5:
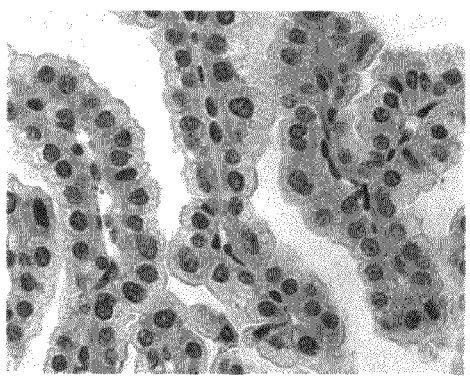
FIG. 5 shows that Intrauterine HK-GBS injection leads to caspase 3 activation in the membranes. 14.5 week timed pregnant mice were injected with either PBS (A) or HK-GBS and euthanized at 5 (B) or 14 hours (C) to isolate the placenta and membranes. Caspase 3 activation was assessed by performing western blotting analysis using an antibody against active-cleaved caspase 3.
Figure 5:
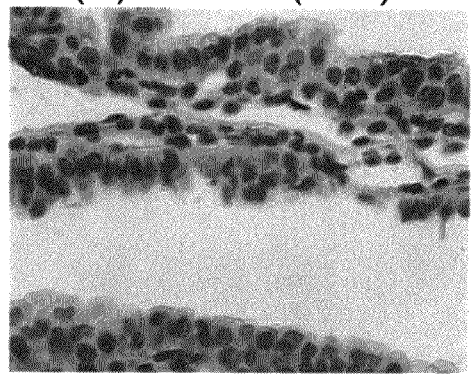
Figure 5:
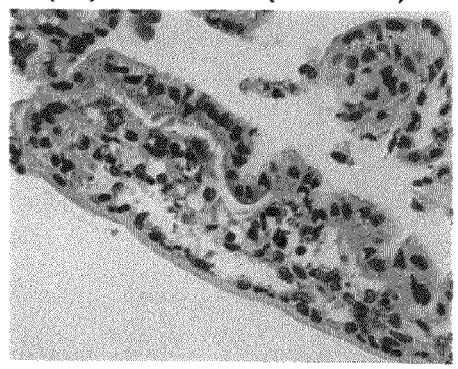
Figure 6:
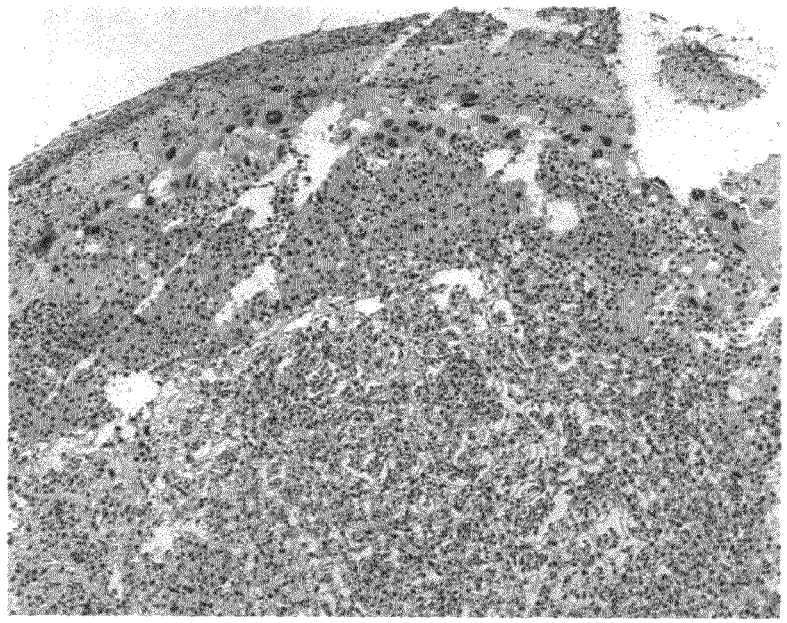
FIG. 6 shows that Intrauterine HK-GBS injection leads to caspase 3 activation in the placenta. In the mouse placenta, similar to the membranes, there were no caspase 3 positive cells at 5 hours as assessed by immunohistochemistry. HK-GBS exposure led to an increase in caspase 3 positive cells above the spongioform trophoblast layer at 14 hours
Figure 7:
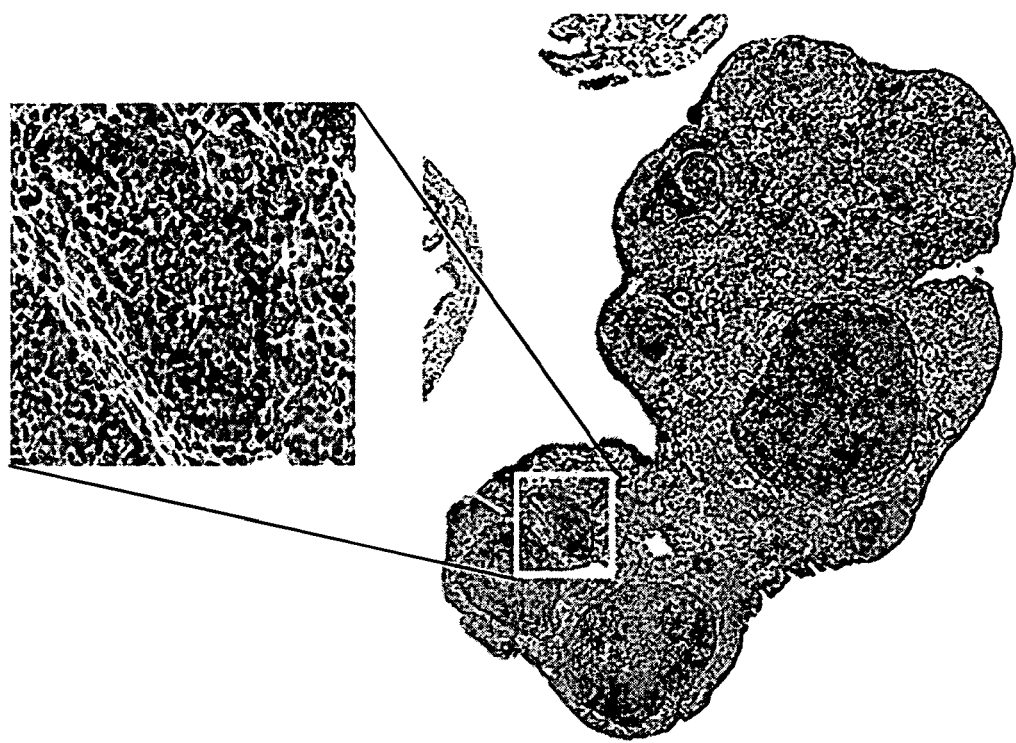
FIG. 7 shows apoptosis in the ovarian follicle. Mouse atretic follicles are known to undergo caspase mediated apoptosis. As anticipated, active caspase 3 expression was detected in the atretic follicles.

Caspase 3 is the common executioner caspase activated by both the extrinsic (Fas) and intrinsic (mitochondrial) caspase machinery. HK-GBS exposure induced caspase 3 expression in the placenta as assessed by western blot (FIG. 3). Caspase 3 was activated in both the membranes (FIG. 4) and placentas (FIG. 5) after 14 hours of exposure as assessed by immunohistochemistry, using an antibody specific for activated caspase 3. In order to confirm the specificity of the caspase 3 staining, we used nonpregnant mouse ovaries as a positive control tissue. As anticipated, caspase 3 was activated in the atretic follicles (FIG. 6).

Pretreatment with Pancaspase Inhibitor Z-VAD-FMK Delays HK-GBS-Induced Preterm Delivery We have previously shown that in vitro pretreatment with Z-VAD-FMK prevented *Chlamydia* heat shock protein (cHSP60)-induced apoptosis in primary human trophoblasts and fibroblasts (Equils et al., 2006). Based upon that observation, we hypothesized that the generalized inhibition of caspases would prevent microbial antigen-induced preterm delivery in the mouse pregnancy model. In order to test this hypothesis we pre-treated day 14.5 pregnant CD1 mice either with Z-VAD-FMK (10 mg/kg dissolved in DMSO/PBS) or with medium intraperitoneally 30 minutes prior to intraperitoneal HK-GBS injection.

Pre-treatment with Z-VAD-FMK significantly delayed preterm delivery at 18 hours (Table 1; p=0.007).

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of treating Group B streptococcus, *Chlamydia trachomatis, Escherichia coli* or mycoplasma infection-associated preterm delivery in a mammal, comprising:
   providing a composition, comprising:
      Z-VAD-FMK, and
      a pharmaceutically acceptable carrier; and
   administering a therapeutically effective amount of the composition to the mammal.

2. The method of claim 1, wherein preterm delivery is treated by inhibition of apoptosis by Z-VAD-FMK.

3. The method of claim 1, wherein the composition also comprises a therapeutically effective amount of an antibiotic.

4. The method of claim 1, further comprising administering a quantity of an antibiotic to the mammal.

5. The method of claim 1, wherein the infection is caused by Group B streptococcus.

6. The method of claim 1, wherein the mammal is a human.

* * * * *